United States Patent [19]
Wideman

[11] 3,975,392
[45] Aug. 17, 1976

[54] PREPARATION OF 3-METHYLPIPERIDINE
[75] Inventor: Lawson G. Wideman, Akron, Ohio
[73] Assignee: The Goodyear Tire & Rubber Company, Akron, Ohio
[22] Filed: June 27, 1975
[21] Appl. No.: 591,184

[52] U.S. Cl. .......................................... 260/293.52
[51] Int. Cl.² ...................................... C07D 295/02
[58] Field of Search ............................... 260/293.52

[56] References Cited
UNITED STATES PATENTS

| | | | |
|---|---|---|---|
| 2,790,804 | 4/1957 | Silverstone | 260/293.52 |
| 3,350,439 | 10/1967 | Feldman et al. | 260/293.52 |

FOREIGN PATENTS OR APPLICATIONS

| | | | |
|---|---|---|---|
| 1,482,577 | 4/1967 | France | 260/293.52 |

Primary Examiner—Norma S. Milestone
Attorney, Agent, or Firm—F. W. Brunner; J. Y. Clowney

[57] ABSTRACT

There is disclosed a process for the preparation of 3-methylpiperidine which comprises a multi-stage hydrogenation of α-methylene glutaronitrile using as a catalyst a highly dispersed nickel in which the first stage hydrogenation is conducted at temperature ranging from about 20°C to about 50°C at hydrogen pressure of at least 14 kilograms per square centimeter to form α-methyl glutaronitrile. The second stage hydrogenation is conducted at temperatures ranging from about 80°C to about 175°C at hydrogen pressures of at least 42 kilograms per square centimeter to form 2-methyl-1,5-diaminopentane. At which time the reaction mixture is cooled to a temperature below the boiling point of any of the materials present in the process and all the excess hydrogen vented off. The temperature is then increased to at least about 150°C to allow the 2-methyl-1,5-diaminopentane to cyclize to form 3-methylpiperidine.

5 Claims, No Drawings

PREPARATION OF 3-METHYLPIPERIDINE

This invention is directed to the preparation of 3-methylpiperidine. More specifically, it is directed to the preparation of 3-methylpiperidine by multi-stage hydrogenation process of α-methylene glutaronitrile using as the sole catalyst a highly dispersed nickel metal such as Raney nickel.

The preparation of 3-methylpiperidine from α-methylene glutaronitrile is not new. In French patent specification 1,482,577, there is disclosed a process whereby 3-methylpiperidine is prepared from α-methylene glutaronitrile by multi-stage hydrogenation process. This prior art process uses in the first stage a catalyst which is 5 percent palladium on carbon. After the first stage hydrogenation is completed, this palladium catalyst is subsequently removed from the hydrogenation mixture and a second catalyst, a Raney cobalt, is employed in a second stage hydrogenation to give 3-methylpiperidine. In the first stage hydrogenation, the temperature employed was about 22°C and hydrogen pressure of about 100.33 kilograms per square centimeter (kg/cm$^2$) was employed. In the second stage hydrogenation the temperature employed was about 100°C and the hydrogen pressure was about 365 atmospheres or 377 kg/cm$^2$.

The present invention provides an improved process whereby only one catalyst system is employed for both the first and second stage hydrogenations thereby avoiding the disadvantage of removing the first stage hydrogenation catalyst from the mixture and adding another catalyst before the second stage hydrogenation is accomplished. The present invention also provides a process whereby much improved selectivities to 3-methylpiperidine are obtained.

In U.S. patent application Ser. No. 520,518 filed Nov. 4, 1974, there is described a process for the preparation of 3-methylpiperidine by a multi-stage hydrogenation of α-methylene glutaronitrile employing as a catalyst a highly dispersed nickel metal, in which the first stage hydrogenation is conducted at temperatures ranging from about 20 to about 50°C and hydrogen pressures of at least 14 kilograms per square centimeter (kg/cm$^2$) and wherein the second stage hydrogenation is conducted at temperatures ranging from about 150°C to about 175°C using hydrogen pressures of at least 42 kg/cm$^2$.

In the first stage hydrogenation of the process of this invention, the α-methylene glutaronitrile is believed to be converted to α-methyl glutaronitrile by conversion of the methylene groups to the methyl groups and in the second stage hydrogenation the α-methyl glutaronitrile is reductively cyclized to form 3-methylpiperidine. These reactions can be set forth as:

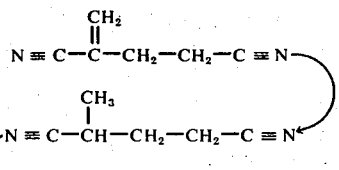

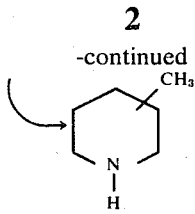

The present invention is an improvement in the method described in U.S. patent application Ser. No. 520,518.

The present invention may be described as follows:

In a process for the preparation of 3-methylpiperidine using a multi-stage hydrogenation of α-methylene glutaronitrile employing as a catalyst a highly dispersed nickel metal, in which the first stage hydrogenation is conducted at temperatures ranging from about 20° to about 50°C and employing hydrogen pressures of at least 200 pounds per square inch gauge (psig) or 14 kilograms per sqare centimeter (kg/cm$^2$) and wherein the second stage hydrogenation is conducted at temperatures ranging from about 80°C to about 175°C and employing hydrogen pressures of at least 600 psig or 42 kg/cm$^2$, the improvement comprising after the uptake of hydrogen ceases in the second stage, reducing the temperature below the boiling point of any of the materials in the process, venting all excess hydrogen and heating the then formed 2-methyl-1,5-diaminopentane to a temperature about 150° to about 175°C for a period of at least 2 hours to cause the cyclization of 2-methyl-1,5-diaminopentane to a 3-methylpiperidine.

The temperature at which the various stages of hydrogenation are conducted have been found to be somewhat critical. In the first stage hydrogenation where the methylene group is converted to a methyl group, the temperature must be controlled from slightly below room temperature to about 50°C. If the temperature is allowed to rise above the 50°C, the α-methylene glutaronitrile tends to polymerize to form an undesirable polymeric material. The first stage reduction of the methylene group of the α-methylene glutaronitrile to the methyl group is accomplished by controlling the temperature in a range from about 20°C to about 50°C and the hydrogen pressure employed is at least 14 kg/cm$^2$. The first stage hydrogenation is controlled under these conditions until the hydrogen uptake ceases when one realizes the methylene group has been converted to a methyl group. At that time, the temperature is raised to a range of from about 150°C to about 175°C and the hydrogen pressure is increased to at least about 42 kg/cm$^2$.

It has been found that the process is best conducted in a solvent system. A variety of solvents may be employed in the process of this invention. The hydrocarbon solvents such as benzene, pentane, and hexane are less preferred because of the poor solubility of α-methylene glutaronitrile in non-polar solvents. An alcohol is the solvent of choice with ethanol being most preferred. The ratio of solvent to α-methylene glutaronitrile should not be too great since it has been observed that a large amount of low boiling by-products are formed at high solvent to reactant ratios. For instance, 20 grams of α-methylene glutaronitrile made up to 400 milliliters volume in ethanol will give an appreciable amount of what is presumably an ethanolic by-product. Similarly, higher boiling by-products will be formed if too little solvent is employed. For instance, if 100 grams of α-methylene glutaronitrile is made up to 200 milliliters volume with ethanol, a high yield of high boiling by-products is formed in the first stage hydrogenation. Therefore, the solvent to α-methylene glutaronitrile weight ratio should vary between about 1/1 to about 3/1.

While it is possible to conduct the hydrogenations of this invention using the α-methylene glutaronitrile (MGN) in the solvent in the absence of any tertiary amine, ammonia or other basic material, it is preferred to employ small amounts of such materials in the system. The use of these basic materials tend to suppress the formation of secondary and/or heavier amines during the hydrogenations. The amounts of the basic material employed depends on the particular one chosen. If an amine is used, large excess of the amine based on the reactant may be used, up to about a weight ratio of amine to MGN of 6/1. If ammonia, the preferred basic material, is employed, the amounts found to be satisfactory would range up to a saturated solution of ammonia in the solvent and MGN at room temperature. If a large excess of ammonia is used, this excess leads to extremely high pressure being developed during the second stage hydrogenation at the higher temperatures therein employed.

Thus, it is usually desirable to conduct the process of the present invention in an alcoholic solvent system which has been made basic by saturating the alcohol solvent/α-methylene glutaronitrile mixture with ammonia.

The pressure of the hydrogen employed in both the first and second stage hydrogenation has not been found to be as critical as the temperatures. No upper limit on the hydrogen pressure of either the first or second stage hydrogenation has been determined. It has been observed, however, that at least 14 kg/cm$^2$ hydrogen pressure should be employed in the first stage hydrogenation. However, due to the exothermic nature of the initial hydrogenation reaction, an excessive hydrogen pressure, is above about 28 kg/cm$^2$, would be a waste. In the second stage hydrogenation, the autogenous vapor pressure, which is in the neighborhood of 31 kg/cm$^2$, when the reaction is conducted at temperatures from about 150° to about 175°C, forces a lower constraint on the hydrogen pressure. Thus, a hydrogen pressure of less than about 35 kg/cm$^2$ tends to give inferior results. Therefore, a preferred hydrogen pressure of at least 42 kg/cm$^2$ is required in the second stage hydrogenation.

The catalyst employed in both the first and the second stage hydrogenation of α-methylene glutaronitrile of this invention is a highly dispersed form of nickel. Raney nickel has been found to be a very good form of highly dispersed nickel for use in the invention. Methods of preparing the Raney nickel catalysts which are useful in this invention are known and can be found in a book entitled "CATALYTIC HYDROGENATION" by Robert L. Augstine published in 1965 by Marcel Dekker, Inc, New York, New York. The procedures employed to prepared Raney nickel do not vary widely and are disclosed in this reference. The author refers to these Raney nickel catalysts as W1, W2, W3, W4, W5, W6, W7 and W8. In addition to the W-type Raney nickel, a Raney nickel referred to as T-1 is preferred or a modification of T-1 Raney nickel is preferred.

In the Journal of Organic Chemistry 26, 1625 (1961), there is described a process for the preparation of what the authors refer to as T-1 Raney nickel by Dominguez, Lopez and Franco. In this article, the authors state that the preparation of the T-1 Raney nickel catalyst is a modification of the procedure described by Papa, Schwenk and Whitman in the Journal of Organic Chemistry 7, 586, (1942) and Papa, Schwenk and Brieger in the Journal of Organic Chemistry, 14, 366, (1949). All of the Raney nickels described in the articles referred to above as operable in the process of this invention.

Other nickel catalysts useful in the invention can be obtained by the use of new techniques known to the catalyst art for depositing metals on suitable supports in a highly dispersed form. These nickel catalysts would exhibit catalytic properties similar to the properties exhibited by the Raney nickel catalysts.

In the article by Dominguez at al, the authors state that the T-1 Raney nickel is prepared as follows:

In a 1-liter 3-neck flask containing 600 ml of a 10 percent sodium hydroxide solution, 40 grams of Raney nickel aluminum alloy (50 percent nickel) was added in small portions over a period of 20 to 30 minutes with mechanical stirring. The temperature being kept during this addition at 90°–95°C. The mixture was stirred for an additional hour period at which time the stirring was stopped and the nickel was allowed to settle, and the solution decanted. The metal was washed with five 200 ml portions of water and then five times with 50 ml of ethanol in such a manner that the nickel was always covered with liquid. The catalyst was then stored under ethanol and refrigerated for further use.

The Raney nickel actually employed in some of the examples of this application and termed by the present inventor as Modified T-1 Raney nickel, was prepared by a slight modification of Dominguez et al's procedure and is as follows:

A solution of 6 grams of sodium hydroxide in 50 ml of water was heated to its boiling point and then there was added 6 grams of Raney nickel aluminum alloy (3 grams of Raney nickel) as rapidly as the hydrogen evolution permits. This mixture was then digested at 95° to 100°C for 1 hour (reflux) and the water was continually replaced as it evaporated. The solution was decanted from the Raney nickel and the metal washed with three 250 ml portions of cold water. This catalyst was employed without further washing with additional ethanol.

The ratio of catalyst to the α-methylene glutaronitrile has not been accurately determined but less than 1 part by weight of the catalyst per 100 parts of α-methylene glutaronitrile leads to inferior results and a catalyst to reactant ratio greater than about 4 parts by weight of nickel to 100 parts of α-methylene glutaronitrile has not been found to be required. Thus, it could be stated that from 1 part by weight of nickel up to 4 parts by weight per 100 parts by weight of α-methylene glutaronitrile could be employed.

The invention is further illustrated by reference to the following examples which are intended to be representative in nature and in no way limiting of the invention.

EXAMPLE 1

A heat-dried, 1-liter stainless steel reactor was flushed with nitrogen and charged with an ethanolic solution (200 ml total volume) containing 50 g of α-methylene glutaronitrile and saturated with anhydrous ammonia (ca. 10 g). The solution contained a suspension of 3 g of the modified T-1 type Raney nickel. The reactor was then charged with hydrogen at about 400 psig or 28.12 kg/cm² at room temperature and the contents of the reactor stirred continuously. The hydrogen pressure was maintained at about 28.12 kg/cm² and the temperature was not allowed to rise above 45°C by employing cooling coils within the reactor. The uptake of hydrogen ceased after about 15 to 30 minutes. The temperature was then raised to 120°C and the reaction pressure was raised to about 600 psig or 42 kg/cm² with hydrogen, and the hydrogen was replaced as it was consumed. The reaction was allowed to continue for 45 minutes at 120°C and at about 600 psig or 42 kg/cm², and then cooled to room temperature. The reactor was vented to zero gauge pressure and reheated to 160°C for 3 hours. The reactor was cooled and the catalyst was filtered from the reaction solution. Gas chromatographic analysis of the reaction mixture on a 50 prime UCW-98 column (programmed from 80°C to 240°C) revealed a quantitative conversion of α-methylene glutaronitrile. The selectivity to 3-methylpiperidine was 92.8 percent.

EXAMPLE II

A reaction was carried under the conditions of Example I, except that the second stage hydrogenation was carried out at 140°C for 30 minutes. Gas chromatographic analysis of the reaction product revealed a quantitative conversion of α-methylene glutaronitrile. The selectivity to 3-methylpiperidine was 88 percent.

EXAMPLE III

A reaction was carried out under the conditions of Example II, except that the reaction time at 160°C was 2 hours. Analysis revealed a quantitative conversion of α-methylene glutaronitrile and an 86 percent selectivity to 3-methylpiperidine, with an 8 percent selectivity to 2-methyl-1,5-diaminopentane.

EXAMPLE IV

A reaction was carried out under the conditions of Example II, except that the reaction time at 140°C was 1 hour and the reaction time at 160°C was 1 hour. Analysis revealed a quantitative conversion of α-methylene glutaronitrile and a 78 percent selectivity to 3-methylpiperidine, with an 18 percent selectivity to 2-methyl-1,5-diaminopentane.

While certain representative embodiments and details have been shown for the purpose of illustrating the invention, it will be apparent to those having skill in this art that various changes and modifications may be made therein without departing from the spirit or scope of the invention.

What is claimed is:

1. In the process for the preparation of 3-methylpiperidine which comprises hydrogenating α-methylene glutaronitrile in a multi-stage hydrogenation employing as a hydrogenation catalyst a highly dispersed nickel catalyst wherein the first stage hydrogenation is conducted at a temperature ranging from about 20° to about 50°C and at a hydrogen pressure of at least about 14 kg/cm² and wherein the second stage hydrogenation is conducted at temperatures ranging from about 150°C to about 175°C and a hydrogen pressure of at least about 42 kg/cm², the improvement comprising after the uptake of hydrogen ceases in the second stage reducing the temperature below the boiling point of any of the materials in the process, venting all excess hydrogen and heating the then formed 2-methyl-1,5-diaminopentane to a temperature 150° to about 175°C for a period of at least 2 hours to cause the cyclization of 2-methyl-1,5-diaminopentane to 3-methylpiperidine.

2. The method according to claim 1 in which the hydrogenations are conducted in an ethanolic solvent solution containing ammonia.

3. The method according to claim 2 in which the catalyst is a Raney nickel.

4. The method according to claim 3 in which the Raney nickel employed is a T-1 type Raney nickel.

5. The method according to claim 3 in which the catalyst employed is a modified T-1 type Raney nickel.

* * * * *